US00PP24163P2

(12) United States Plant Patent
Sonobe

(10) Patent No.: US PP24,163 P2
(45) Date of Patent: Jan. 14, 2014

(54) ***DRACAENA* PLANT NAMED 'SCARLET IBIS'**

(50) Latin Name: *Dracaena concinna*
Varietal Denomination: Scarlet Ibis

(76) Inventor: Yasuhiro Sonobe, Koga (JP)

( * ) Notice: Subject to any disclaimer, the term of this patent is extended or adjusted under 35 U.S.C. 154(b) by 78 days.

(21) Appl. No.: 13/385,752

(22) Filed: Mar. 5, 2012

(51) Int. Cl.
*A01H 5/00* (2006.01)

(52) U.S. Cl.
USPC ..... Plt./383

(58) Field of Classification Search
USPC ..... Plt./383
See application file for complete search history.

(56) References Cited

PUBLICATIONS

PLUTO Plant Variety Database 2013-02 search for Scarlet Ibis.*

* cited by examiner

*Primary Examiner* — Annette Para
(74) *Attorney, Agent, or Firm* — C. A. Whealy

(57) ABSTRACT

A new and distinct cultivar of *Dracaena* plant named 'Scarlet Ibis', characterized by its upright plant habit with foliage initially erect to somewhat outwardly arching; moderately vigorous growth habit; long lanceolate leaves that are dark red and dark greyed purple in color; and good keeping quality and garden performance.

1 Drawing Sheet

Botanical designation: *Dracaena concinna.*
Cultivar denomination: 'SCARLET IBIS'.

BACKGROUND OF THE INVENTION

The present invention relates to a new and distinct *Dracaena* plant, botanically known as *Dracaena concinna* and hereinafter referred to by the name 'Scarlet Ibis'.

The new *Dracaena* plant is a naturally-occurring whole plant mutation of the *Dracaena concinna* 'Rainbow', not patented. The new *Dracaena* plant was discovered and selected by the Inventor from within a population of plants of 'Rainbow' in a controlled greenhouse environment in Otsutsumi, Ibaraki-prefecture, Japan in March, 1999.

Asexual reproduction of the new *Dracaena* plant by cuttings in Otsutsumi, Ibaraki-prefecture, Japan since March, 1999 has shown that the unique features of this new *Dracaena* plant are stable and reproduced true to type in successive generations.

SUMMARY OF THE INVENTION

Plants of the new *Dracaena* have not been observed under all possible environmental conditions and various cultural practices. The phenotype may vary somewhat with variations in environmental conditions such as temperature and light intensity, without, however, any variance in genotype.

The following traits have been repeatedly observed and are determined to be the unique characteristics of 'Scarlet Ibis'. These characteristics in combination distinguish 'Scarlet Ibis' as a new and distinct *Dracaena* plant:

1. Upright plant habit with foliage initially erect to somewhat outwardly arching.
2. Moderately vigorous growth habit.
3. Long lanceolate leaves that are dark red and dark greyed purple in color.
4. Good keeping quality and garden performance.

Plants of the new *Dracaena* differ from plants of the parent, 'Rainbow', primarily in leaf color as plants of 'Rainbow' have red and greyed orange variegated leaves.

Plants of the new *Dracaena* can be compared to plants of the *Dracaena concinna* 'Bicolor', not patented. In side-by-side comparisons conducted in Otsutsumi, Ibaraki-prefecture, Japan, plants of the new *Dracaena* differed primarily from plants of the 'Bicolor' in the following characteristics:

1. Plants of the new *Dracaena* had longer leaves than plants of 'Bicolor'.
2. Leaves of plants of the new *Dracaena* and 'Bicolor' differed in color as plants of 'Bicolor' had pale green-colored leaves.

BRIEF DESCRIPTION OF THE PHOTOGRAPH

The accompanying photograph illustrates the overall appearance of the new *Dracaena* plant showing the colors as true as it is reasonably possible to obtain in colored reproductions of this type. Colors in the photograph may differ slightly from the color values cited in the detailed botanical description which accurately describe the colors of the new *Dracaena* plant. The photograph comprises side perspective view of a typical plant of 'Scarlet Ibis' grown in a container.

DETAILED BOTANICAL DESCRIPTION

The aforementioned photograph and following observations and measurements describe plants grown during the spring in 15-cm containers in a glass-covered greenhouse in Koga-shi, Ibaraki-prefecture, Japan and under environmental conditions and cultural practices which approximate those generally used in commercial *Dracaena* plant production. During the production of the plants, day temperatures averaged 14.5° C. and night temperatures averaged 10° C. Plants were ten months old when the photographs and the botanical description were taken. In the following description, color references are made to The Royal Horticultural Society Colour Chart, Fifth Edition, except where general terms of ordinary dictionary significance are used.

Botanical classification: *Dracaena concinna* 'Scarlet Ibis'.

Parentage: Naturally-occurring whole plant mutation of *Dracaena concinna* 'Rainbow', not patented.

Propagation:

*Type*.—By cuttings.

*Time to initiate roots, summer*.—About 15 days at soil temperatures of about 28° C.

*Time to initiate roots, winter*.—About 30 days at soil temperatures of about 20° C.

*Time to produce a rooted young plant, summer*.—About 20 days at soil temperatures of about 28° C.

*Time to produce a rooted young plant, winter*.—About 40 days at soil temperatures of about 20° C.

*Root description*.—Thick, fibrous; creamy white in color.

*Rooting habit*.—Moderately freely branching; medium density.

Plant description:

*Plant and growth habit*.—Upright plant habit with foliage initially erect to somewhat outwardly arching; narrow inverted triangle; moderately vigorous growth habit.

*Plant height*.—About 45.8 cm.

*Plant diameter or spread*.—About 42.2 cm.

*Internode length*.—About 6.7 mm.

*Stem color*.—Close to 148C.

*Stem strength*.—Strong.

Foliage description:

*Orientation*.—Initially erect to somewhat outwardly arching.

*Arrangement*.—Alternate, simple; sessile.

*Length*.—About 32 cm.

*Width*.—About 1 cm.

*Shape*.—Lanceolate.

*Apex*.—Acuminate.

*Margin*.—Entire.

*Texture, upper and lower surfaces*.—Smooth, glabrous.

*Venation pattern*.—Parallel.

*Color*.—Developing leaves, upper and lower surfaces: Close to 137B; stripes and spots, close to 149D. Fully expanded leaves, upper surface: Close to 53B; stripes and spots, close to 187B. Fully expanded leaves, lower surface: Close to 142A; stripes and spots, close to 187B. Venation, upper and lower surfaces: Similar to surface coloration.

Flower description: Flower initiation and development has not been observed on plants of the new *Dracaena.*

Disease & pest resistance: Plants of the new *Dracaena* have not been shown to be resistant to pathogens and pests common to *Dracaena.*

Keeping quality: Excellent keeping quality; plants of the new *Dracaena* are durable and will maintain good leaf substance indefinitely.

Garden performance: Plants of the new *Dracaena* have been observed to have good garden performance and to tolerate wind, rain and temperatures ranging from about 5° C. to 35° C.

It is claimed:

1. A new and distinct *Dracaena* plant named 'Scarlet Ibis' as illustrated and described.

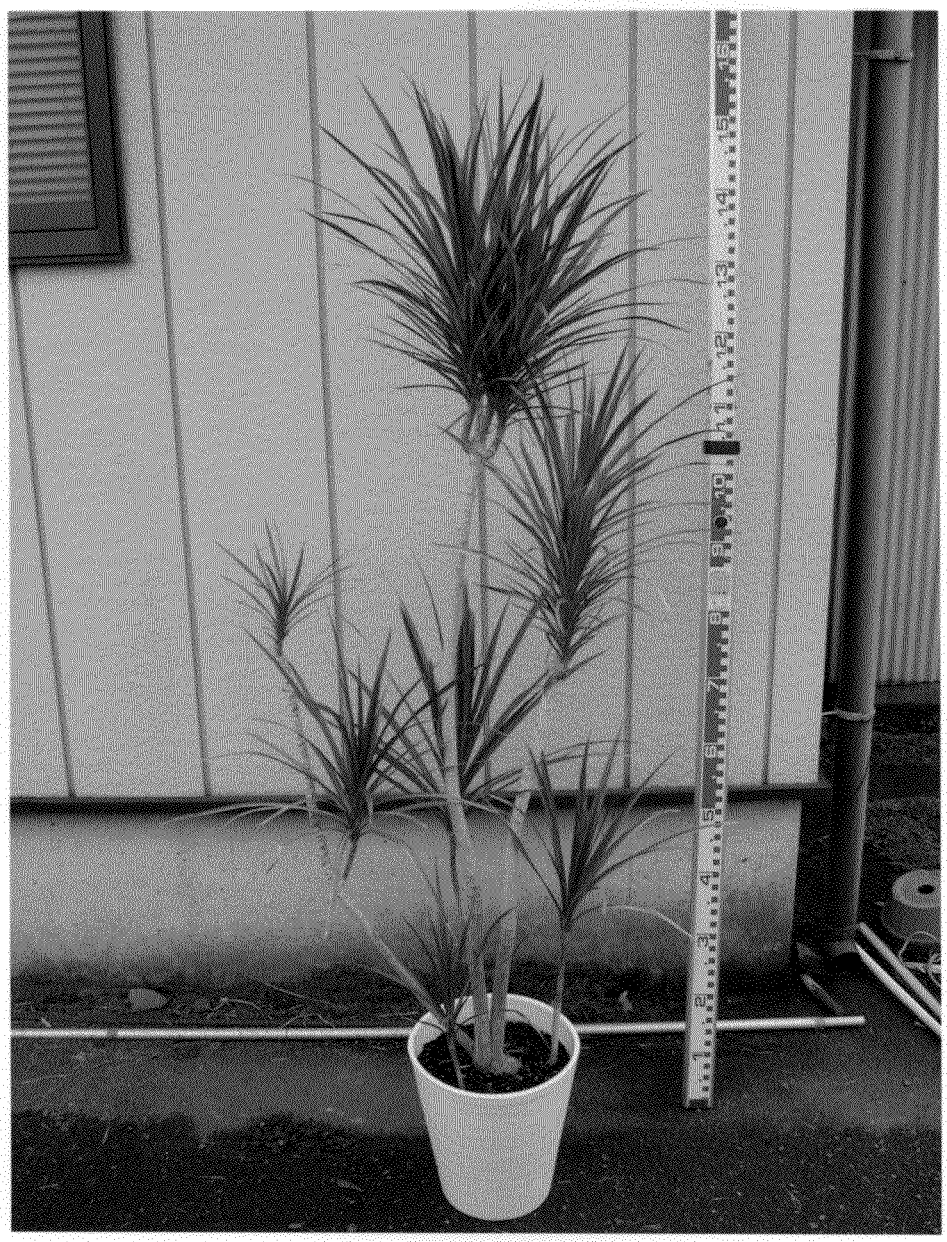

* * * * *